United States Patent
Lew et al.

(10) Patent No.: US 11,840,499 B2
(45) Date of Patent: Dec. 12, 2023

(54) BIOBASED-FATTY ACID ARGINATES

(71) Applicant: The United States of America, as represented by the Secretary of Agriculture, Washington, DC (US)

(72) Inventors: Helen N Lew, Wynnewood, PA (US); Xuetong Fan, North Wales, PA (US); Kun Huang, Conshohocken, PA (US); Jianwei Zhang, Guangdong Province (CH)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 98 days.

(21) Appl. No.: 17/186,958

(22) Filed: Feb. 26, 2021

(65) Prior Publication Data

US 2022/0274918 A1 Sep. 1, 2022

Related U.S. Application Data

(60) Provisional application No. 62/983,113, filed on Feb. 28, 2020.

(51) Int. Cl.
*A01N 47/44* (2006.01)
*C07C 279/14* (2006.01)

(52) U.S. Cl.
CPC ............ *C07C 279/14* (2013.01); *A01N 47/44* (2013.01)

(58) Field of Classification Search
CPC .............................. C07C 279/14; A01N 47/44
See application file for complete search history.

(56) References Cited

U.S. PATENT DOCUMENTS 8,604,073 B2 * 12/2013 Ming ..................... A61K 31/43
514/642

* cited by examiner

*Primary Examiner* — Benjamin J Packard
(74) *Attorney, Agent, or Firm* — John D. Fado; Maria Restrepo-Hartwig (57) ABSTRACT

A biobased fatty acid arginate may be synthesized according to the disclosed process by combining arginine and a fatty acid. The fatty acid arginate may have certain beneficial properties, such as surfactant properties or acting as an antimicrobial agent.

9 Claims, 12 Drawing Sheets

BIOBASED-FATTY ACID ARGINATES

REFERENCE TO RELATED APPLICATIONS

This application claims the benefit of U.S. Provisional Application No. 62/983,113 filed Feb. 28, 2020, which is incorporated herein by reference in its entirety.

BACKGROUND

In recent decades, there have been numerous investigations regarding antimicrobial agents, which can be used in the food industry, cosmetics, coatings, and personal care products. Because of their prevalence, the study of such agents is one of the most important topics in both chemistry and biology. Pathogenic microorganisms are a threat to human health since they can cause severe infectious diseases, and in order to inactivate these pathogens, numerous antimicrobial agents have been developed. However, the effect of any one specific antimicrobial agent can vary as against different bacteria or other microorganisms. Moreover, some microorganisms have the potential to evolve and gain antimicrobial resistance. This threat has become a global one and has worsened over the last few decades due to the overuse or misuse of antibiotics. Further, most extant antimicrobials are synthetic agent and there has been growing concern about the potential negative impact of these synthetic compounds on health. Therefore, there is an urgent need for new harmless and environmentally friendly antimicrobial agents.

There are already thousands of antimicrobial agents that have been extracted from plants and synthesized via chemical reactions. When developing a new antimicrobial agent, sustainability and toxicity are two of the most crucial properties to be considered. Instead of using petroleum-based materials, sustainable bio-based materials are more attractive. Toxicity is even more important when they are used in food or personal care products. Ethyl lauroyl arginate (LAE) is an example of a commercial antimicrobial derived from natural components, lauric acid, L-arginine, and ethanol. The active ingredient is ethyl-$N^\alpha$-lauroyl-L-arginate HCl, the hydrochloride salt of an N-fatty acyl-substituted amino acid ethyl ester. It is a broad-spectrum antimicrobial against most food-borne pathogens.

There is a need for a new family of antimicrobials that can mimic LAE but with improved capabilities against target microbes.

All of the references cited herein, including U.S. Patents and U.S. Patent Application Publications, are incorporated by reference in their entirety.

Mention of trade names or commercial products in this publication is solely for the purpose of providing specific information and does not imply recommendation or endorsement by the U.S. Department of Agriculture.

SUMMARY

According to at least one exemplary embodiment, a compound may have the following formula:

(1)

where R is a linear or branched aliphatic chain of length C6-C24, and has at least one of an alkyl or a phenolic group substituent.

According to further embodiments of the invention, R may have a length of C6, C7, C8, C9, C10, C11, C12, C13, C14, C15, C16, C17, C18, C19, C20, C21, C22, C23, or C24, and may be one of oleic arginate, isooleic arginate, stearic arginate, or isostearic arginate.

According to another embodiment, a microbe may be killed using an effective amount of the disclosed compound. Alternatively, or in addition, the growth of a microbe may be inhibited using an effective amount of the disclosed compound. Effective amounts of the disclosed compound may be determined using routine methods known in the art.

According to another embodiment, a method of producing a fatty acid arginate may include halogenation of a non-phenolic fatty acid to create a halogenated fatty acid and argination of the halogenated fatty acid by reacting the halogenated fatty acid with arginine to create a fatty acid arginate. According to a further embodiment, a method of producing a phenolic fatty acid arginate may include protecting a hydroxyl group on a phenol group of a phenolic fatty acid to create a prepared phenolic fatty acid, halogenation of the prepared phenolic fatty acid to create a halogenated phenolic fatty acid, argination of the halogenated phenolic fatty acid by reacting the halogenated fatty acid with an arginine source to create a protected phenolic fatty acid arginate, and deprotecting the hydroxyl group to create a phenolic fatty acid arginate.

BRIEF DESCRIPTION OF THE FIGURES

Advantages of embodiments of the present invention will be apparent from the following detailed description of the exemplary embodiments. The following detailed description should be considered in conjunction with the accompanying figures in which.

Exemplary

Exemplary

Exemplary

Exemplary

Exemplary

Exemplary

Exemplary

Exemplary

Exemplary

Exemplary

Exemplary

Exemplary

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Unless defined otherwise, all technical and scientific terms used herein have the same meaning as commonly understood by one of ordinary skill in the art to which the invention belongs. As used herein, the term "about" refers to a quantity, level, value, or amount that varies by as much as 30%, preferably by as much as 20%, and more preferably by as much as 10% to a reference quantity, level, value, or amount. Although any methods and materials similar or equivalent to those described herein can be used in the practice or testing of the present invention, the preferred methods and materials are now described.

Other compounds may be added to the composition provided they do not substantially interfere with the intended activity and efficacy of the composition; whether or not a compound interferes with activity and/or efficacy can be determined, for example, by the procedures utilized below.

The amounts, percentages, and ranges disclosed herein are not meant to be limiting, and increments between the recited amounts, percentages, and ranges are specifically envisioned as part of the invention.

"Optional" or "optionally" means that the subsequently described event or circumstance may or may not occur, and that the description includes instances in which said event or circumstance occurs and instances where it does not. For example, the phrase "optionally comprising X" means that the composition may or may not contain X, and that this description includes compositions that contain and do not contain X.

The term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) which is not specifically disclosed herein.

According to at least one exemplary embodiment, a fatty acid arginate may be synthesized according to the disclosed process. The fatty acid arginate may have certain beneficial properties, such as surfactant properties or acting as an antimicrobial.

A fatty acid arginate according to the present invention may have the following chemical structure in formula (1):

(1)

In formula (1) above, R is a linear or branched aliphatic chain of length C6-C24 with at least one of an alkyl or phenolic group substituent. For example, R may include phenolics as those disclosed in U.S. Pat. No. 10,071,946, such as phenol, thymol, carvacrol, creosol, guaiacol, hydroxybenzoic acid, gallic acid, vanillic acid or the like. Such phenolic groups have one or more hydroxyl groups on the aromatic ring. They may also have other substituents on the hydroxyl aromatic ring including alkyl groups which can be a saturated or unsaturated or conjugated straight chain, a saturated, unsaturated or conjugated branched chain, cyclic and/or aromatic.

These phenolic compounds may also include additional functional groups to the hydroxyl aromatic ring such as amino (—$NH_2$), secondary amino (—NR'H; where R'=alkyl groups which can be a saturated, unsaturated or conjugated straight chain, a saturated or unsaturated or conjugated branched chain, cyclic and/or aromatic), tertiary amino (—NR'R"; R' and R"=alkyl groups which can be a saturated, unsaturated or conjugated straight chain, a saturated or unsaturated or conjugated branched chain, cyclic and/or aromatic), carboxylic acid (—R'$CO_2$H; R'=alkyl groups which can be a saturated, unsaturated or conjugated straight chain, a saturated or unsaturated or conjugated branched chain, cyclic and/or aromatic, esters (—'RCOOR"; R',R"=alkyl groups which can be a saturated, unsaturated or conjugated straight chain, a saturated or unsaturated or conjugated branched chain, cyclic and/or aromatic), ethers (—OR'; R'=alkyl groups which can be a saturated, unsaturated or conjugated straight chain, a saturated or unsaturated or conjugated branched chain, cyclic and/or aromatic), halogens (fluoro ($F^-$), chloro ($Cl^-$), bromo ($Br^-$), iodo)), ($I^-$)), hydroxyl (—OH), oxygen, nitrogen, sulfonyl (—$SO_2$—) and thiol (—S—) substituents.

The phenolics which may be used also include but are not limited to cresol, 2,6-ditert-butylphenol, 2,6-ditert-butyl-4-methylphenol, 2,6-ditert-butyl-4-ethylphenol, anisole, and the like; (2) two or more adjacent R groups may be joined, forming a multi-ring structure, these rings may or may not be aromatic, as in the cases of 2-hydroxynaphthalene and tocopherols, respectively, and can be homo- or heterocyclic. In addition, other compounds may be used include those with 2 or 3 hydroxyl group on the ring (such as catechol, gallic acid, caffeic acid) and those with additional aldehyde and acid groups (such as coumaric acid and syringic acid). Economically, the preferred phenolics will be relatively cheaper phenolics such as simple phenol, hydroxybenzaldehyde, carvacrol, thymol, vanillin, or vanillic acid.

In synthesizing a fatty acid arginate according to the present invention, a fatty acid may first be halogenated. Optionally, in the case of a fatty acid with a phenolic group, the hydroxyl group of the phenol may be protected prior to halogenation. Halogenation may be achieved, for example, by chlorination. The halogenated fatty acid can then be reacted with an arginine source to achieve a fatty acid arginate. In the case of having protected the hydroxyl group on a phenol, deprotection can then be done to create the final product.

A fatty acid arginate (FAA) according to the present invention may be used in one or more of several ways. For example, an FAA may be used as a surfactant, or as an antimicrobial agent. When used as a surfactant, a desired amount of the FAA may be added to a solution. When used as an antimicrobial agent, an effective amount for killing or inhibiting the growth of a microbe may be applied to a surface, an object, in an area, or directly to the target microbe wherever it resides. An effective amount may be determined by known and standard means in the art.

Example 1

Synthesis of Fatty Acid Arginates

Fatty acids were first converted to fatty acid chlorides, and then reacted with L-arginine ethyl ester dihydrochloride to create the disclosed compounds. Both fatty acids with and without phenolic groups were used.

Preparation of Fatty Acid Chloride Without Phenolic Groups

Fatty acid (5.0 g of oleic acid or iso-oleic acid) was dissolved in dichloromethane (10 mL) and transferred in a three-neck round bottom flask equipped with a condenser. The mixture was placed in an ice bath to chill for a couple minutes, and then thionyl chloride (2.5 mL, 2.0 equivalents to fatty acid) was added via a syringe. The reaction was refluxed for 5 h. When the reaction was completed and cooled, the residual thionyl chloride and dichloromethane were removed through a base trap (i.e., sodium hydroxide packed with glass wool) connected to a vacuum line. The fatty acid chloride was obtained as a viscous yellowish liquid at >99% yield.

Preparation of Fatty Acid Chloride With Phenolic Groups

This production method is different due to the need of hydroxyl protection of the phenol group.

Poly-PBC-FA (phenolic branched chain-fatty acid) (5.0 g of oleic phenol, soy phenol, or soy thymol) was transferred into a 50 mL round bottom flask. With gently magnetic stirring, acetic anhydride (1.0 equivalent to oil, 1.36 g) was added followed by addition of a catalytic amount of boron trifluoride etherate (1 mol %, 18.8 mg) via a syringe. The mixture was stirred for 1 hour at room temperature or up to 80° C. After completion of the reaction, the mixture was extracted with ethyl acetate/water three times. The organic phase was then washed by saturated sodium chloride solution. The crude product was obtained by removing the organic solvent using rotary evaporator and then purified by column chromatography. The purified product was used as a precursor for poly-PBC-FA-chloride, which is prepared according to the same procedure as the fatty acid-chloride without phenolics, given above.

Preparation of Fatty Acid Arginate (FAA)

L-arginine ethyl ester dihydrochloride (1.0 equivalent to the fatty acid-chloride) and 10 mL of anhydrous dimethylformamide (DMF) was transferred into a 50 mL round bottom flask. Triethylamine (3.0 equivalent to the fatty acid chloride) was then added directly to the mixture. Subsequently, with vigorous stirring, the fatty acid chloride was added to the flask dropwise via a funnel. A small amount of anhydrous DMF was used to rinse the funnel to make sure all the fatty acid chloride was added. The flask was sealed and the reaction was stirred at room temperature for 15 minutes and then heated at 50° C. for 2 h. The mixture was dissolved in ethyl acetate (20 mL), filtered through celite in a packed funnel to remove the triethylamine hydrochloride salt under vacuum, and the filtrate was then transferred to a 250 mL separatory funnel. 50 mL of cold water (15° C.) was used to wash the filtrate in order to remove the residual triethylamine. The organic phase was then extracted with distilled water twice, followed by saturated sodium chloride solution. The crude product was obtained by removing the organic solvent using rotary evaporator. Flash silica gel column chromatography was used to purify the fatty acid-arginate (FAA) product.

Deprotection

For the protected phenolic FAA, deprotecting was achieved by dissolving 1.0 g of the purified hydroxyl protected phenolic-branched-chain fatty acid arginate in 10 mL of anhydrous ethanol and transferring into a 250 mL round bottom flask equipped with a condenser. With gentle stirring, 5 mL of triethylamine was added to the mixture via a pipette. The mixture was refluxed for 2 h, and then the ethanol and triethylamine were removed by rotary evaporator to obtain the final product.

Other Modifications

Other modifications can be made to the FAA. For example, unsaturated linear-chain FAA can be converted to saturated linear FAA through a general hydrogenation step.

Example 2

Structure Characterization of FAAs

ATR-FT-IR

Figure 2:
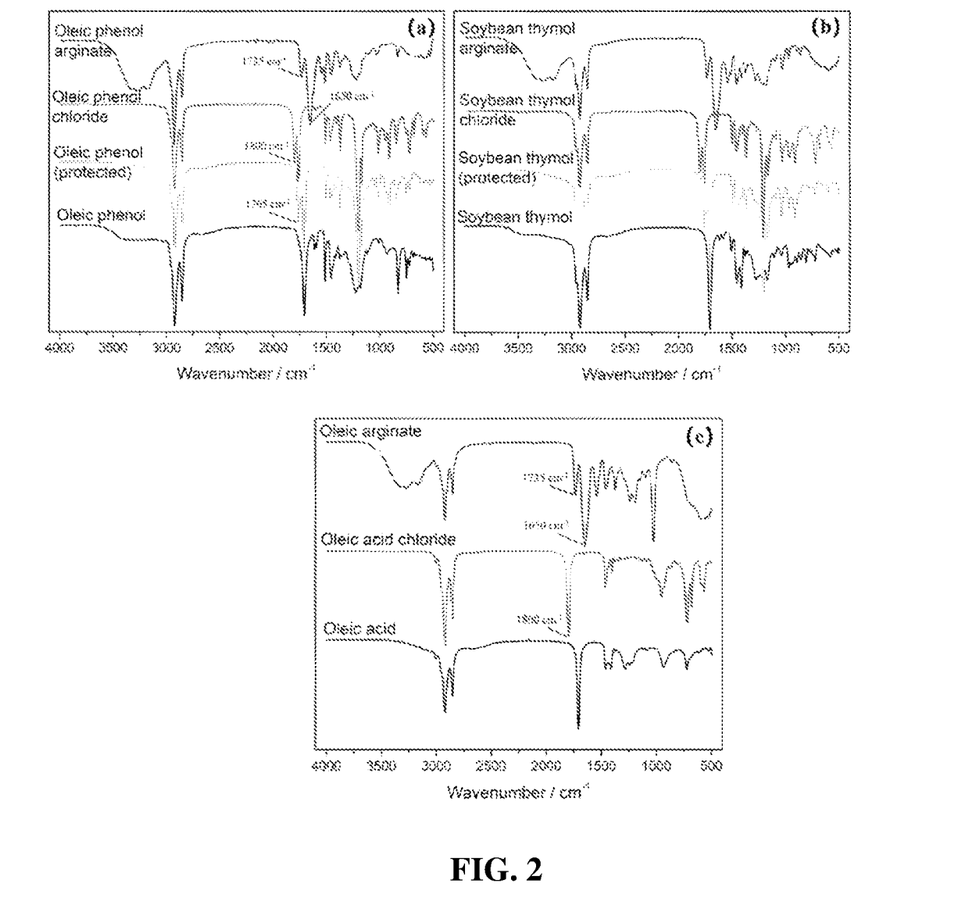
FIG. 2 shows attenuated total reflectance-Fourier transform-infrared (ATR-FT-IR) spectra for fatty acid feedstocks, intermediates, and final products according to the present invention.
Figure 3A:
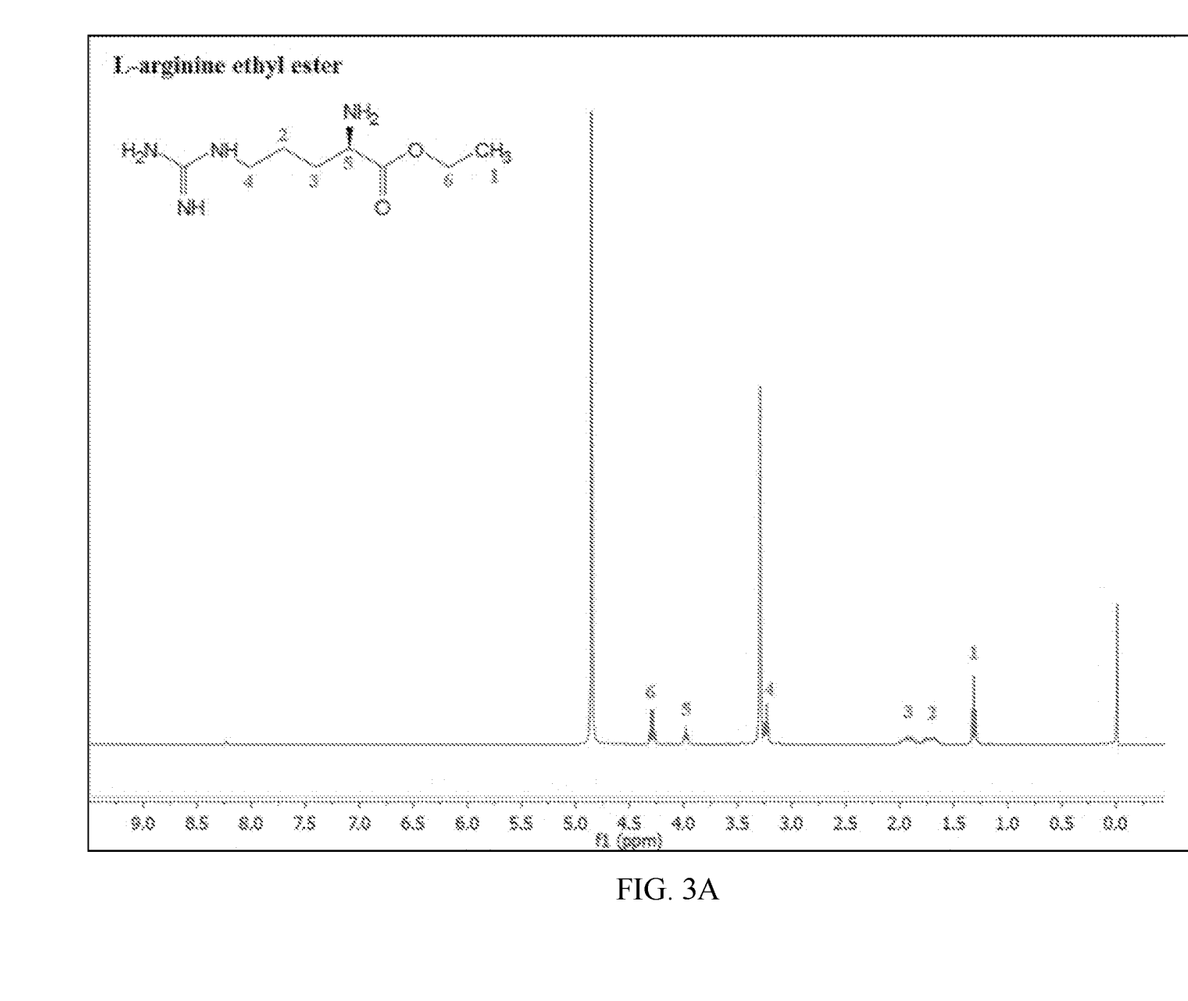
FIG. 3A shows an NMR spectrum of an arginine source as used in the present invention.
Figure 3B:
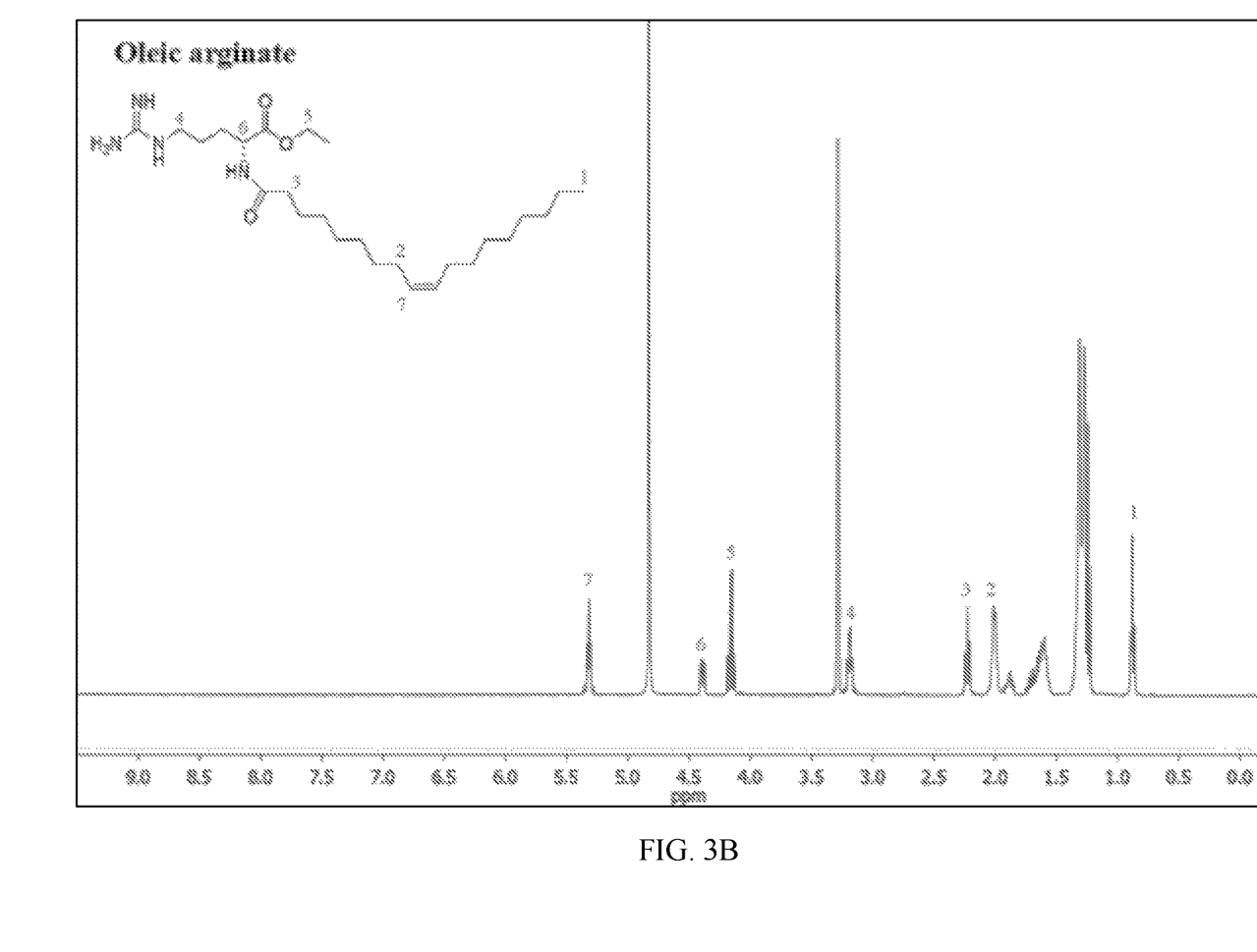
FIG. 3B shows an NMR spectrum of oleic arginate, a product produced according to the present invention.
Figure 3C:
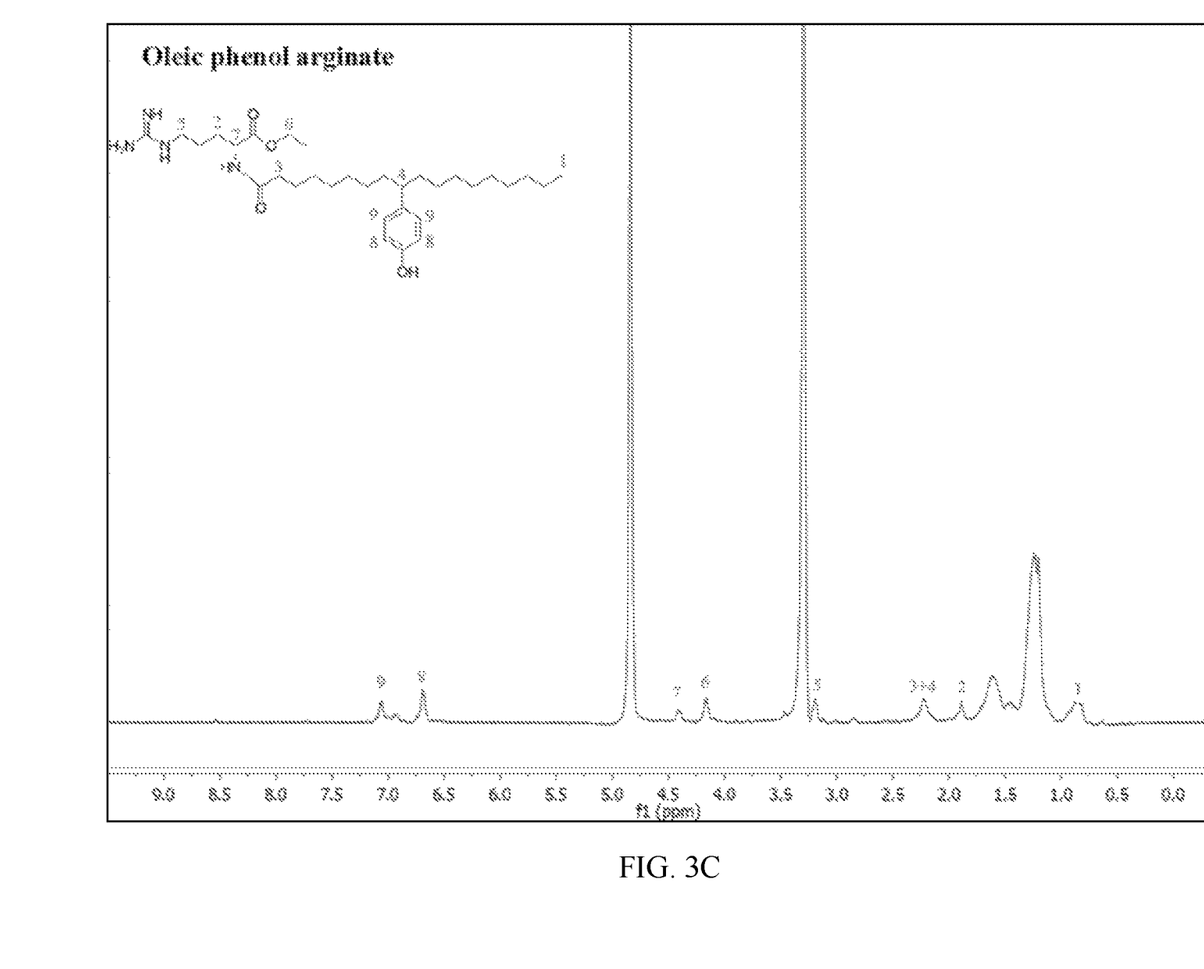
FIG. 3C shows an NMR spectrum of oleic phenol arginate, a product produced according to the present invention.
Figure 3D:
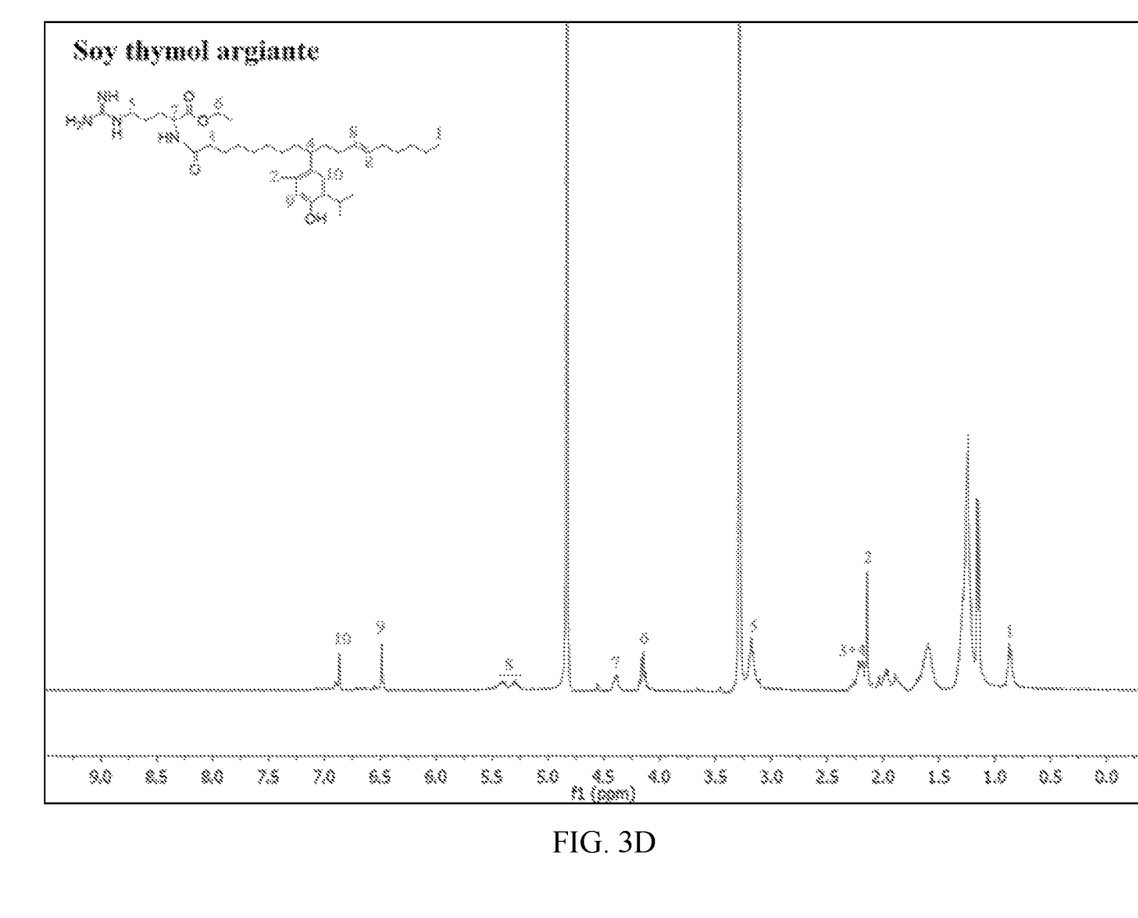
FIG. 3D shows an NMR spectrum of soy thymol arginate, a product produced according to the present invention.
Figure 4A:
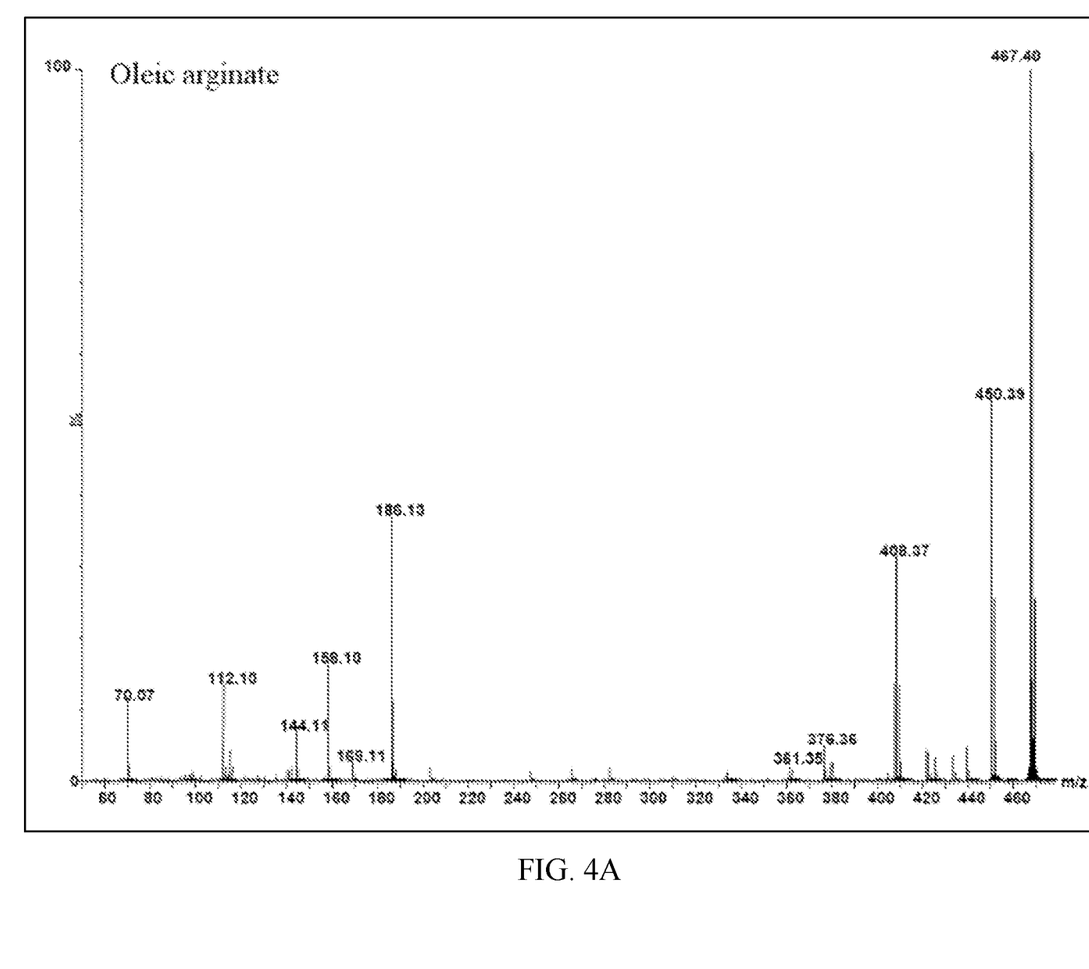
FIG. 4A shows an LC-MS spectrum of oleic arginate, a product produced according to the present invention.
Figure 4B:
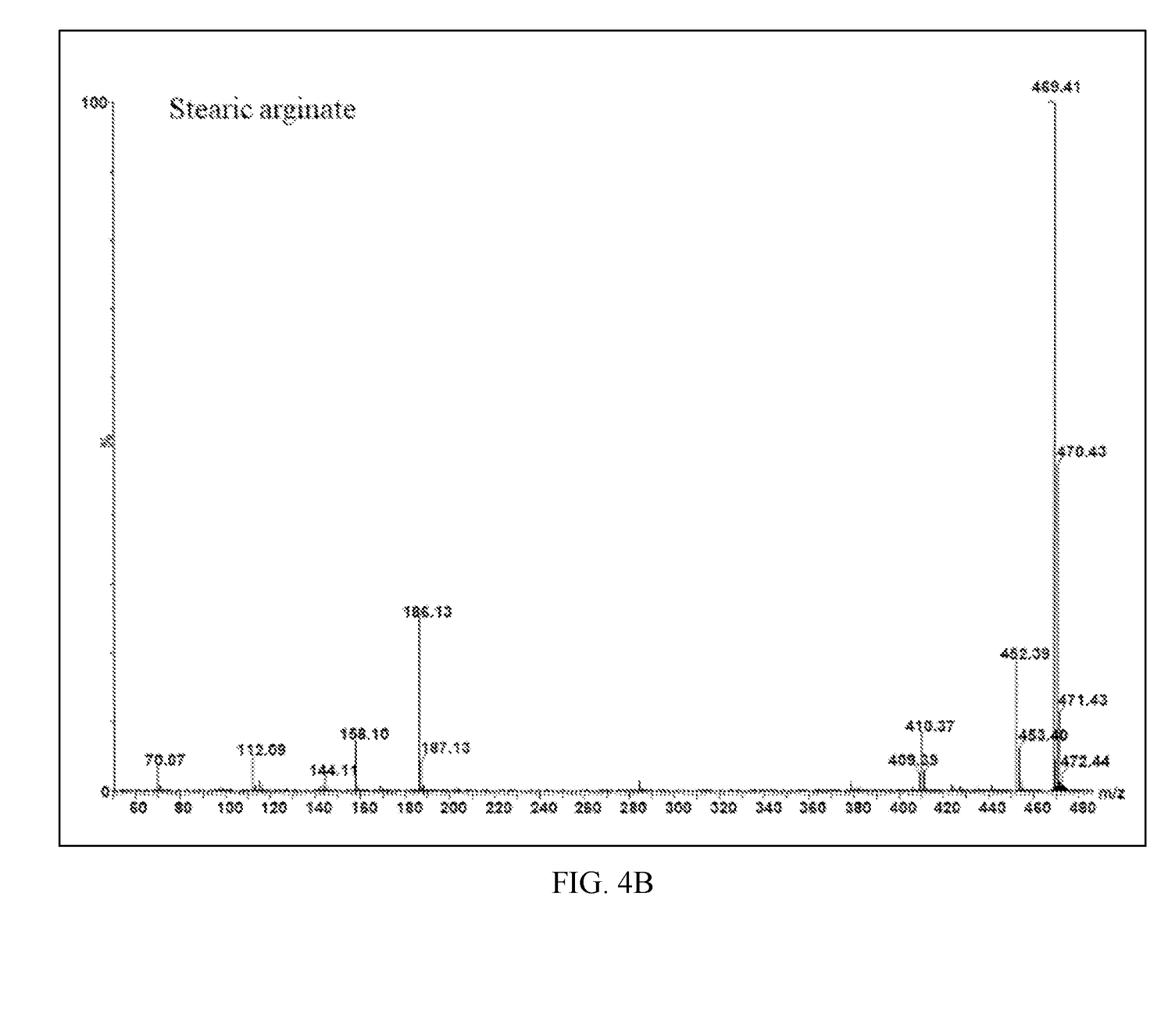
FIG. 4B shows an LC-MS spectrum of stearic arginate, a product produced according to the present invention.
Figure 4C:
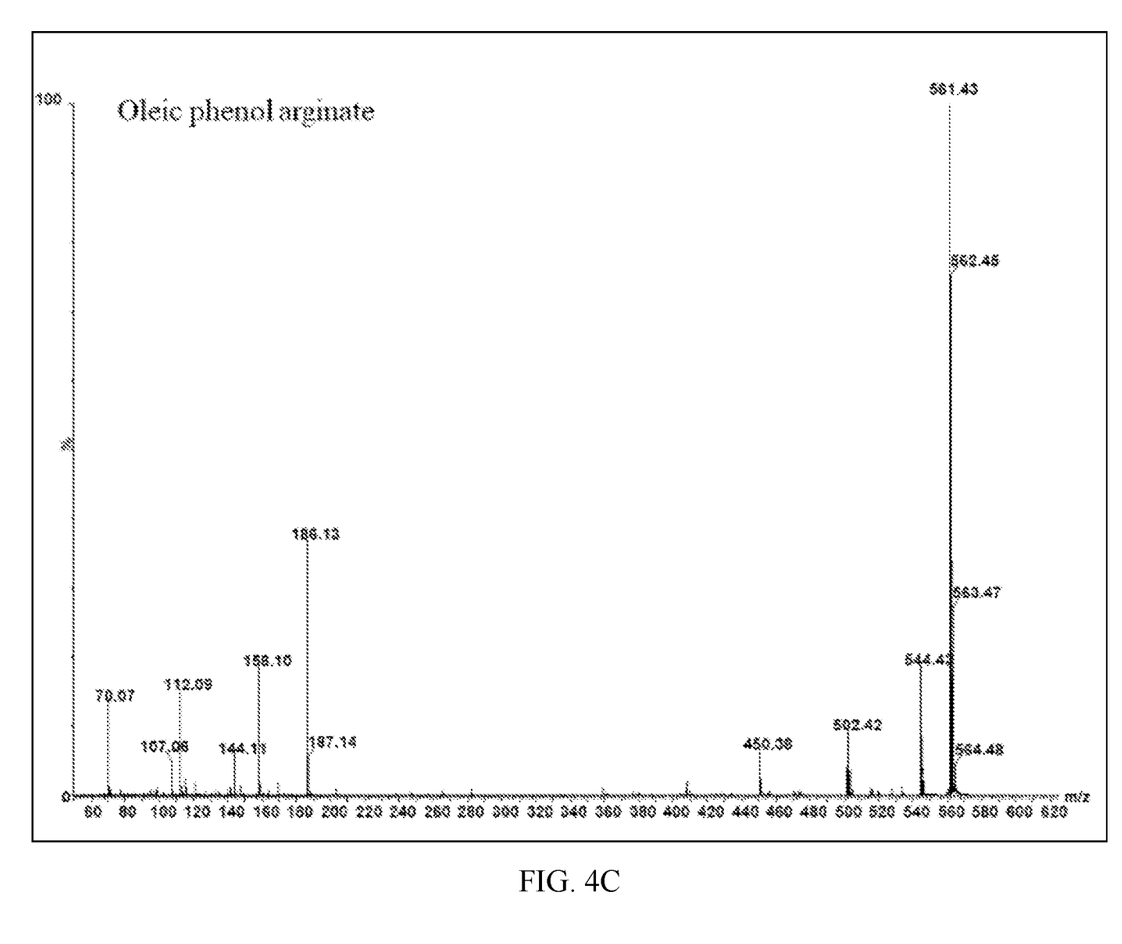
FIG. 4C shows an LC-MS spectrum of oleic phenol arginate, a product produced according to the present invention.
Figure 4D:
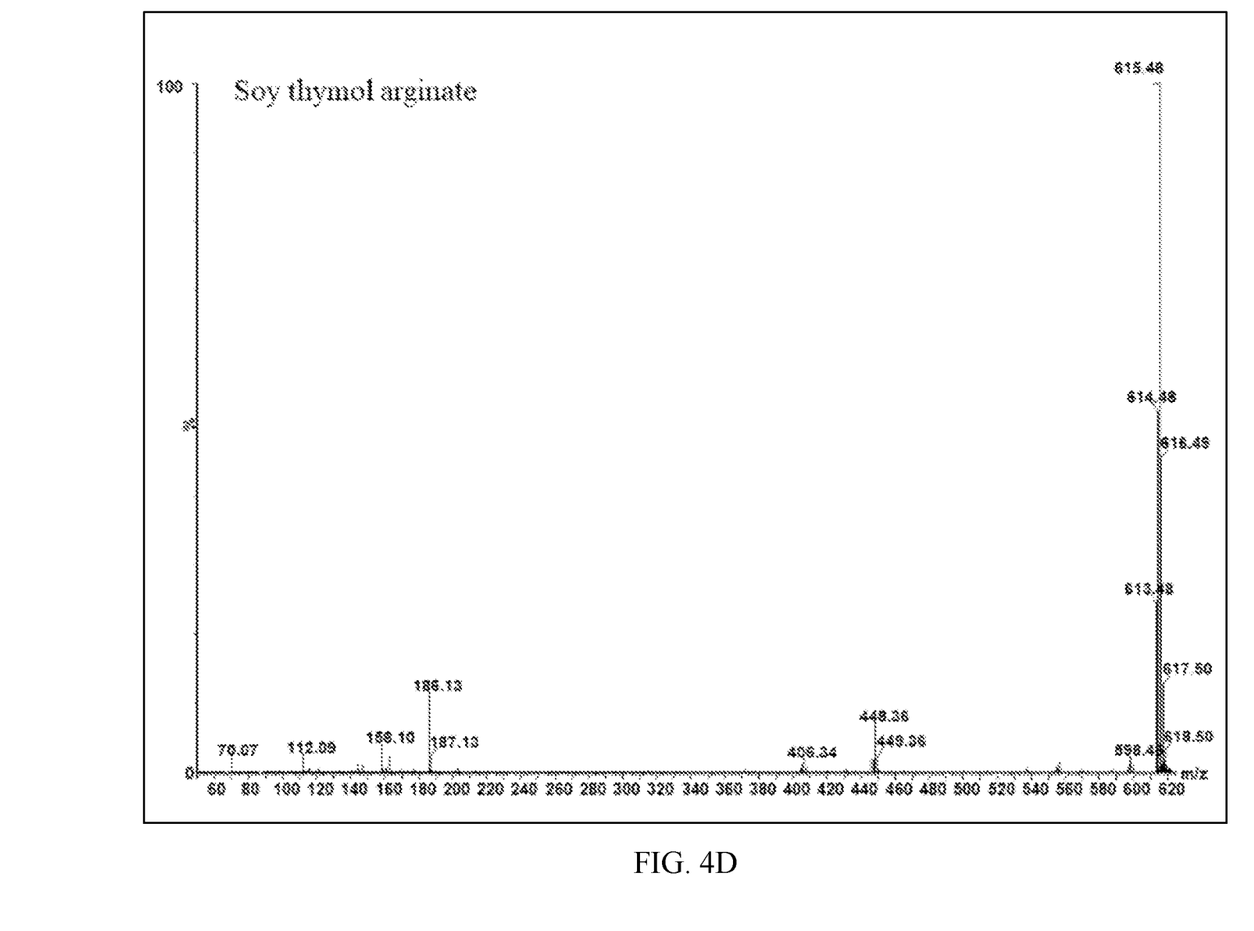
FIG. 4D shows an LC-MS spectrum of soy thymol arginate, a product produced according to the present invention.

Attenuated total reflectance-Fourier transform-infrared spectroscopy (ATR-FT-IR) was done according to the method in Ngo (2014. Improved zeolite regeneration processes for preparing saturated branched-chain fatty acids. Eur. J. Lipid Sci. Technol. 116, 645-652). The ATR-FT-IR spectra for three different feedstocks, and the related intermediates and FAA products, are shown in FIG. 2. From the spectra of poly-PBC-FA-arginates (in (a) and (b) of FIG. 2), obvious differences are found between the spectra of the feedstock and the hydroxyl protected product. After the protection of the hydroxyl group, a peak at 1765 $cm^{-1}$ appears to indicate the carbonyl of the protection group. On the spectrum of the oleic phenol-chloride, the peak at 1800 $cm^{-1}$ is attributed to the carbonyl of fatty acid-chloride (Cl—C=O), and the peak at 1707 $cm^{-1}$ that corresponds to the carbonyl of carboxylic group (HO—C=O) completely disappears, which implies the fatty acid has been converted to fatty acid-chloride while the protection group is intact because the peak at 1765 cm$^{-1}$ remains the same. Finally, on the spectrum of the final arginate product, a broad peak at 3100-3600 cm$^{-1}$ is observed. This is attributed to the amine group from the arginine. The peaks at 1735 cm$^{-1}$ and 1650 cm$^{-1}$ indicate the carbonyl of ethyl ester group (CH$_3$CH$_2$O—C=O) and amide bond (NH—C=O), respectively. For the case of oleic-arginate or iso-oleic-arginate, the ATR-FT-IR spectra show a similar pattern except that there is no hydroxyl protected intermediate involved.

NMR

For NMR analysis, all samples were analyzed by solution state proton ($^1$H) spectroscopy recorded on a 14 Tesla Agilent NMRS DD2 spectrometer. Deuterated methanol was used as solvent to dissolve the samples and their spectra were measured at 25° C. The $^1$H spectra had spectral widths of 12 ppm, and were acquired with a 45° pulse angle using a 5 or 10 s relaxation delay. Inverse-gating of the broad-band proton-decoupling was used to avoid non-uniform enhancement of carbon signals due to proton NOE effects. The residual $^{13}$C resonance of the solvent was used as the internal chemical shift reference for these 1D spectra.

In the $^1$H-NlMR of the raw material (L-arginine ethyl ester), the spectrum (FIG. 3, (a)), shows two shifts at 3.95 ppm and 4.30 ppm, which are the chemical shifts of two characteristic hydrogens, the adjacent hydrogen (CH—C=O) of the amide bond on the arginine backbone and the methylene hydrogen (O—CH$_2$CH$_3$) of ethyl group. On the $^1$H-NMR spectrum of oleic-arginate (FIG. 3, (b)), the chemical shifts of the two characteristic hydrogens have moved to 4.42 ppm and 4.15 ppm, respectively. The reaction has formed an amide bond, whose electron cloud had a deshielding effect on the neighboring hydrogen. Therefore, the chemical shift of this hydrogen has moved downfield (from 3.95 ppm to 4.42 ppm). On the other hand, the carbonyl group has an electron induced effect on the methylene hydrogen, which enhances the shielding effect and the chemical shift moves upfield. Additionally, the amide bond is far away from these hydrogen atoms, so the effect on chemical shift is insignificant (from 4.30 ppm to 4.15 ppm). The chemical shift of the hydrogen adjacent to the amide bond on the oleic acid carbon chain is 2.22 ppm. The signal of the hydrogen on the unsaturated carbon appears at 5.32 ppm. The characteristic peaks in the $^1$H-NMR spectrum (FIG. 3, (c)) of oleic phenol-arginate are the same as those of oleic arginate except for the absence of the peaks in the range of 5.0-5.5 ppm, which indicate that there is no unsaturated carbon bond. Another difference is the signal in the range of 6.8-7.2 ppm, which indicates the chemical shifts of the hydrogen atoms on the aromatic ring. This proves the successful combination of the poly-PBC-FA with arginine. The number of aromatic hydrogen atoms of soy thymol-arginate is less than that of oleic-phenol-arginate and soy-phenol-arginate, so the peaks in the range of 6.8-7.2 ppm are relatively smaller (FIG. 3, (d)). The signal at 2.14 ppm is the chemical shift of methyl hydrogen adjacent to the aromatic ring. And there is a peak in the range of 5.2-5.5 ppm, indicating that there is an unsaturated bond on its carbon chain. Moreover, the random positions of the unsaturated bond make it a broad peak, which is the aggregation from the signal of different isomers.

Further NMR analysis indicated other isomers are formed in the soy thymol reaction product. Some isomers, due to the placement of functional groups, would likely have stearic hinderance to certain reactions and/or other functionalities, whereas others would not have this issue.

LC-MS

Liquid chromatography-mass spectrometry (LC-MS) analysis was achieved using a liquid chromatographer equipped with a column set at 45° C. and running the following gradient at 80 μL/min: initial time to 2 min water:acetonitrile, 50:50; ramped up to a linear gradient at 10 min of water:acetonitrile, 5:95, and returning to the initial conditions at 15 min. with 10 min equilibration time between injections. The solvents contained 0.1% formic acid. The column was connected to a quadrupole time of flight mass spectrometer running in positive mode with an electrospray probe. Capillary voltage was set to 3 KV, temperature at 350° C., and cone voltage at 40V. The collision energy was set a 6 eV for MS and ramped between 10 and 30 eV for MS/MS.

The LC-MS results (FIG. 4) further confirmed the chemical structures of the reaction products. Notable characteristic peaks seen include m/z=186.13 for the arginine fragment [C$_8$H$_{16}$N$_3$O$_2$], m/z=112.09 for [C$_5$H$_{10}$N$_3$$^+$], and m/z=70.07 for [C$_4$H$_8$N$^+$].

Summary

Figure 1A:
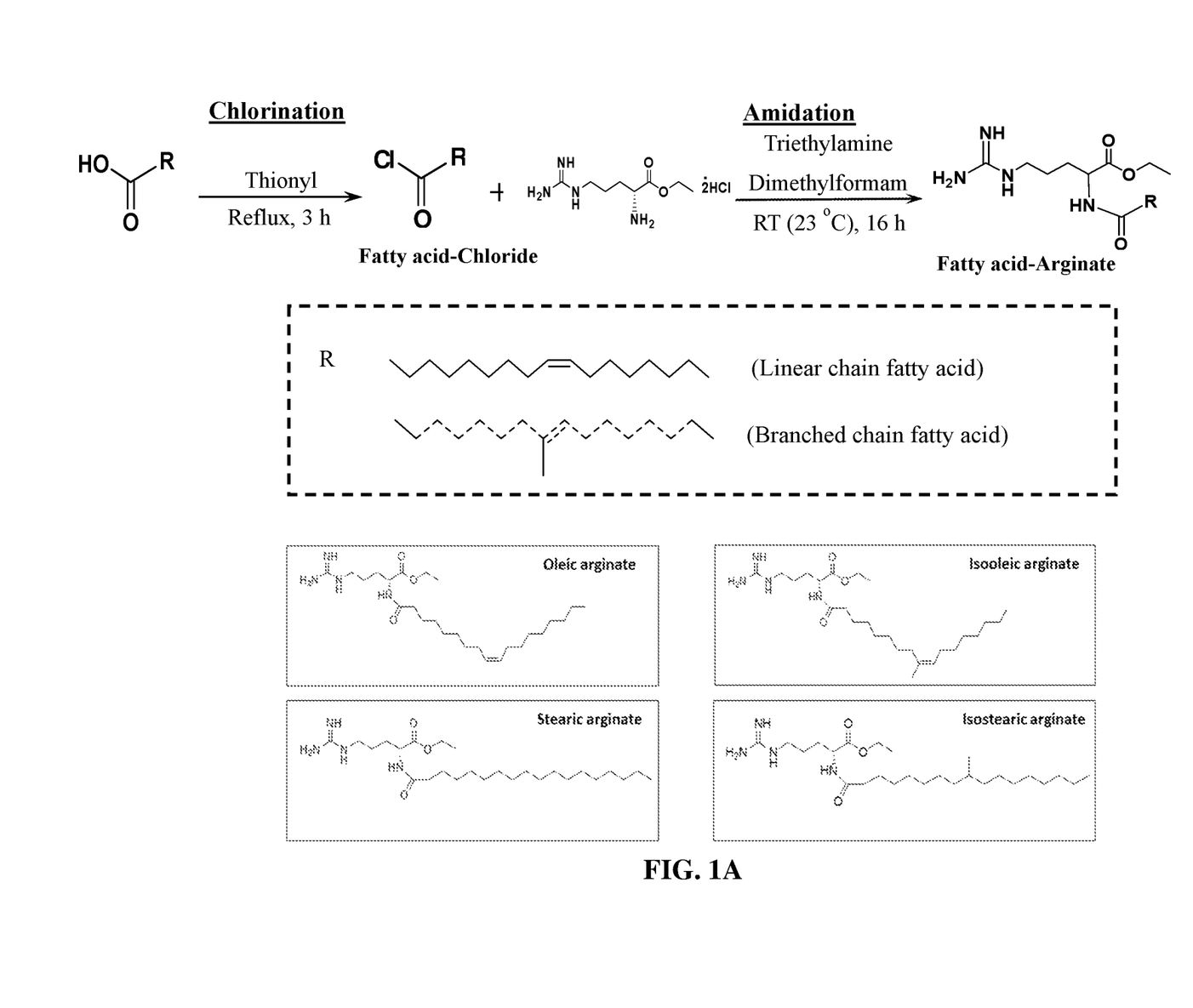
FIG. 1A shows a scheme for creating fatty acid arginates according to the present invention when the fatty acid does not comprise a phenolic group.
Figure 1B:
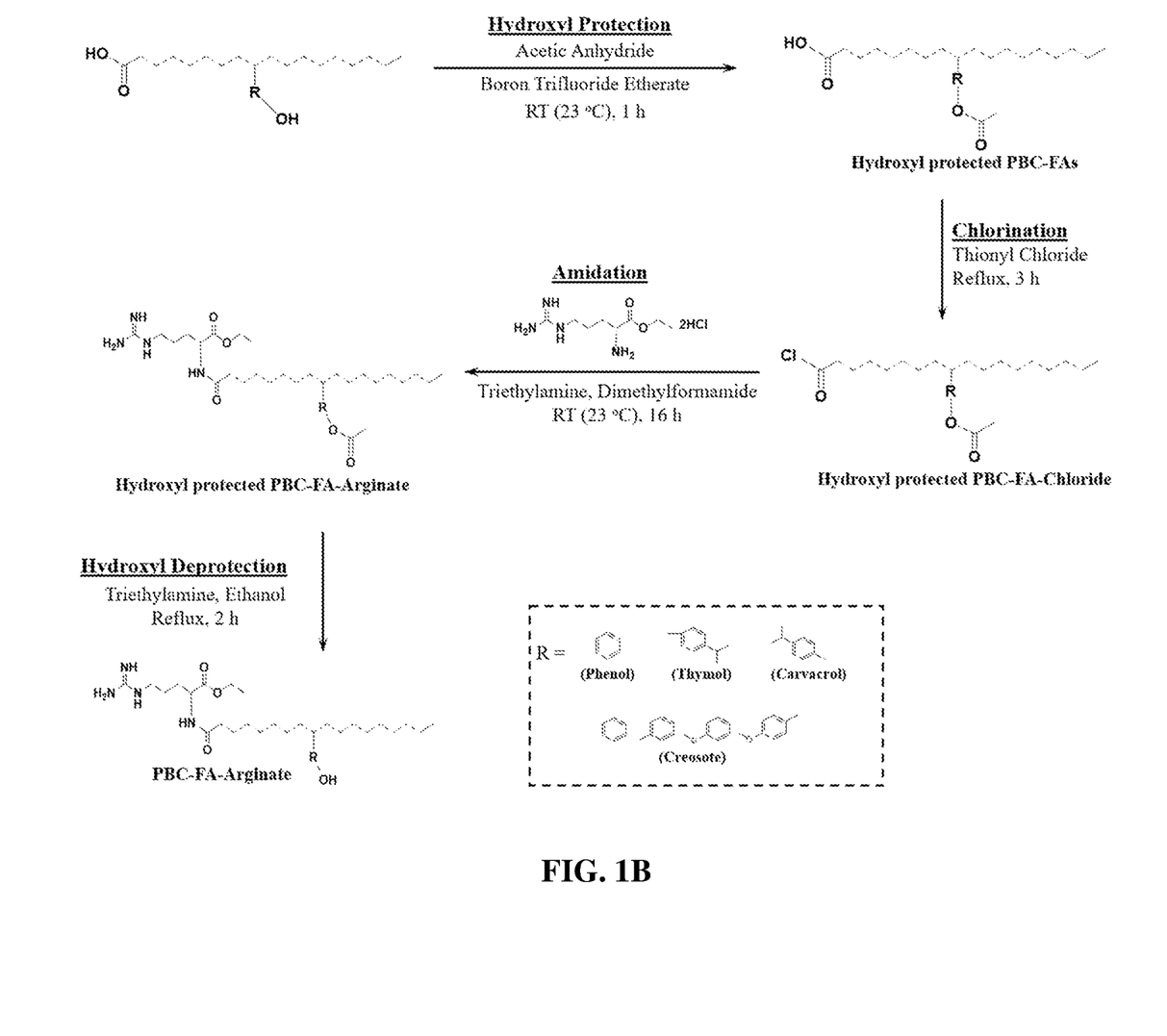
FIG. 1B shows a scheme for creating fatty acid arginates according to the present invention when the fatty acid does comprise a phenolic group.

The above characterizations confirmed the structures of the products as shown in FIGS. 1A and 1B.

Example 3

Surfactant Properties of FAAs

Samples of the analyte were weighed and dissolved in distilled water to make a 10 mM stock solution. The stock solution was then subsequently diluted to make 5 mM, 1 mM, 0.5 mM, 0.25 mM, 0.125 mM, and 0.0625 mM solutions. The series of solutions were used to measure the surface tension using a drop image method with a surface tension instrument. Measurement for each sample was done in triplicate and the average value was calculated. Critical micelle concentration (CMC) is the concentration above which micelles form in the surfactant solution.

Figure 5:
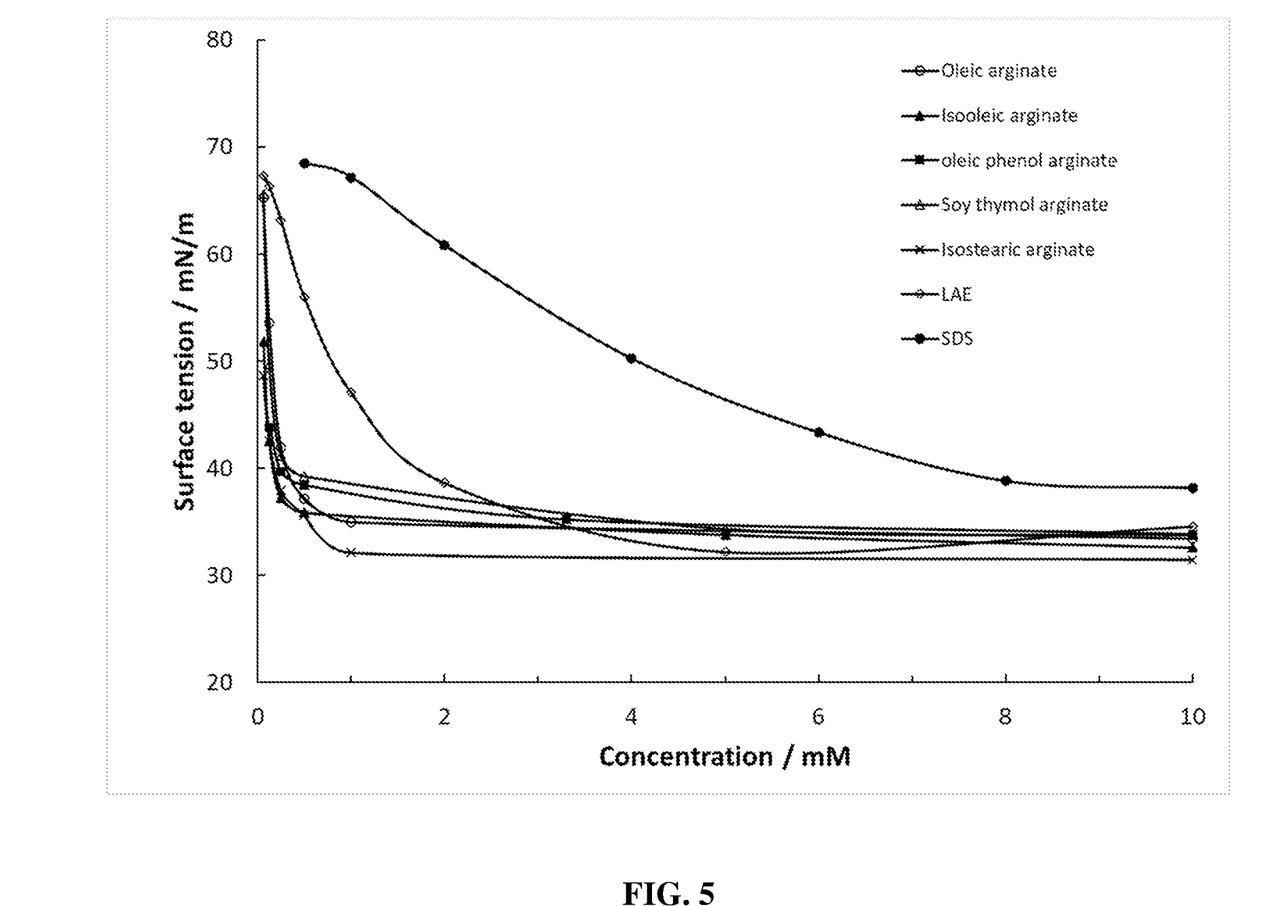
FIG. 5 shows surfactant properties of fatty acid arginates.

The commercial product LAE (Ambeed; Arlington Heights, IL) is known as an effective surfactant due to its hydrophilic amine group and hydrophobic acyl chain and was used as a benchmark against which to measure the usefulness of the arginates. The surfactant tensions of the aqueous solution of the synthesized compounds with different concentrations were measured (FIG. 5). As expected, the synthesized arginates showed strong ability in lowing the surface tension. With increasing surfactant concentration, the surface tension decreased to a certain level (32-34 mN/m). Compared to LAE, the synthesized arginates had much lower CMC values. This means that similar surface tension can be achieved with less of the synthesized arginates than LAE. Data was also collected for another commonly used surfactant, SDS. The CMC of SDS is much higher than LAE and the synthesized arginates. Additionally, with the surfactant concentration increase, the surface tension can only drop down to 38 mN/m, which indicated the efficacies of the synthesized arginates were stronger than that of SDS.

Example 4

Antimicrobial Properties of FAAs

Antimicrobial activity studies were performed using standard methods. For all compounds, at least 3 independent replicates of quadruplicate tests were conducted. The minimum inhibitory concentration (MIC) was determined as the lowest test compound concentration for which no color change (no active growth) occurred. Minimum bactericidal concentration (MBC) was determined by spreading 100 μl from each growth-negative well onto TSA and incubating at 37° C. for 24 h. MBC was the MIC where no viable growth occurred. The results are shown in Table 1 below:

TABLE 1

Antimicrobial data for various analytes.
All MICs and MBCs are given in ppm

|  | L. innocua | | E. coli | |
| --- | --- | --- | --- | --- |
|  | MIC | MBC | MIC | MBC |
| Ethyl lauroyl arginate | 7.3 | 14.5 | 7.3 | 7.3 |
| L-arginine (commercial) | >232.7 | >232.7 | >232.7 | >232.7 |
| L-arginine ethyl ester dihydrochloride | >232.7 | >232.7 | >232.7 | >232.7 |
| Oleic acid | >232.7 | >232.7 | >232.7 | >232.7 |
| Isooleic acid | >232.7 | >232.7 | >232.7 | >232.7 |
| Oleic arginate | 3.6 | 3.6 | 116.4 | 116.4 |
| Isooleic arginate | 1.8 | 1.8 | >232.7 | >232.7 |
| Stearic arginate | 14.5 | 29.1 | >232.7 | >232.7 |
| Isostearic arginate | 3.6 | 7.3 | >232.7 | >232.7 |
| Oleic branched chain phenol | 3.6 | 7.3 | >232.7 | >232.7 |
| Soy branched chain thymol | 14.5 | 29.1 | >232.7 | >232.7 |
| Oleic phenol arginate | 1.2 | 5.0 | >232.7 | >232.7 |
| Soy thymol arginate | 3.6 | 14.5 | >232.7 | >232.7 |

Except for oleic phenol and soy thymol, the other raw materials or precursors, such as L-arginine, L-arginine ethyl ester dihydrochloride, and oleic and isooleic acid, did not show any inhibition against Gram-positive *Listeria innocua* (ATCC 33090), as the MIC and MBC were higher than 232.7 ppm. Contrarily, the synthesized fatty acid arginates showed significant antimicrobial activities. Among them, the MBC values of oleic arginate and isooleic arginate were 3.6 ppm and 1.8 ppm, respectively. Those of stearic arginate and isosteric arginate were 29.1 and 7.3, respectively. This indicated that the arginine derivatives synthesized with unsaturated fatty acids (oleic acid, isooleic acid) appear to have stronger antimicrobial activity than those synthesized with saturated fatty acids (stearic acid). However, the MBC values of oleic phenol arginate and soy thymol arginate are 5.0 ppm and 14.5 ppm, respectively. Although they contained a phenolic group, their antimicrobial activities are slightly weaker than that of oleic arginate.

On the other hand, in the test of Gram-negative *Escherichia coli* (ATCC 700728), except that oleic arginate showed a weak activity, the other fatty acid arginates had no antimicrobial activity (MIC and MBC were higher than 232.7 ppm).

It is noted that through the use of both MIC and MBC tests, both the ability to kill microbes and the ability to inhibit growth of microbes was tested.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A chemical composition comprising a compound of the following formula:

wherein R is a linear or branched aliphatic chain of length C6-C24, and has at least one of an alkyl or a phenolic group substituent.

2. The composition of claim 1, wherein R is a linear or branched aliphatic chain of length C6-C24, and optionally has at least one of an alkyl or a phenolic group substituent.

3. The composition of claim 1, wherein the compound is one of oleic arginate, isooleic arginate, stearic arginate, or isostearic arginate.

4. The composition of claim 1, wherein R has an alkyl substituent.

5. The composition of claim 1, wherein R has a phenolic group substituent.

6. A method of killing a microbe comprising exposing said microbe to an effective amount of the composition of claim 1.

7. A method of inhibiting growth of a microbe on an object or in an area comprising applying an effective amount of the composition of claim 1 to said object or area.

8. A method of producing a fatty acid arginate, the method comprising:
   halogenation of a non-phenolic fatty acid to create a halogenated fatty acid; and
   argination of the halogenated fatty acid by reacting the halogenated fatty acid with arginine to create a fatty acid arginate.

9. A method of producing a phenolic fatty acid arginate, the method comprising:
   protecting a hydroxyl group on a phenol group of a phenolic fatty acid to create a prepared phenolic fatty acid;
   halogenation of the prepared phenolic fatty acid to create a halogenated phenolic fatty acid;
   argination of the halogenated phenolic fatty acid by reacting the halogenated fatty acid with an arginine source to create a protected phenolic fatty acid arginate; and
   deprotecting the hydroxyl group to create a phenolic fatty acid arginate.

\* \* \* \* \*